(12) United States Patent
Brinker et al.

(10) Patent No.: US 8,434,378 B2
(45) Date of Patent: May 7, 2013

(54) DISSOLUTION-TESTING VESSEL COVER

(75) Inventors: Jeffrey Brinker, Westfield, NJ (US);
Timothy John Nadolski, North Brunswick, NJ (US)

(73) Assignee: Distek, Inc., North Brunswick, NJ (US)

( * ) Notice: Subject to any disclaimer, the term of this patent is extended or adjusted under 35 U.S.C. 154(b) by 104 days.

(21) Appl. No.: 13/085,064

(22) Filed: Apr. 12, 2011

(65) Prior Publication Data

US 2011/0247435 A1  Oct. 13, 2011

Related U.S. Application Data

(60) Provisional application No. 61/323,150, filed on Apr. 12, 2010.

(51) Int. Cl.
*G01N 33/00* (2006.01)

(52) U.S. Cl.
USPC .............................................. 73/866

(58) Field of Classification Search ........................ None
See application file for complete search history.

(56) References Cited

U.S. PATENT DOCUMENTS

| | | | |
|---|---|---|---|
| 3,935,318 A * | 1/1976 | Mihailide | 426/80 |
| 4,141,461 A | 2/1979 | LaChance | |
| 4,203,527 A | 5/1980 | LaChance, Sr. | |
| 4,550,850 A | 11/1985 | Smith et al. | |
| 5,064,086 A | 11/1991 | McEntee | |
| 2006/0260421 A1 | 11/2006 | Sekizawa et al. | |
| 2006/0260423 A1 | 11/2006 | Sekizawa et al. | |
| 2009/0029472 A1 | 1/2009 | Chattaraj et al. | |

FOREIGN PATENT DOCUMENTS

| | | |
|---|---|---|
| EP | 0 366 629 A1 | 5/1990 |
| JP | 2004-0351257 A | 12/2004 |
| JP | 2007024743 A | 2/2007 |
| WO | 2004055209 A1 | 7/2004 |
| WO | 2009076231 A1 | 6/2009 |
| WO | WO 2011/081857 A1 | 7/2011 |

OTHER PUBLICATIONS

"Quality Lab Accessories (QLA) Product Catalog," http://www.qla-llc.com, 2007 [retrieved on Apr. 5, 2011]. Retrieved from the Internet: <URL: http://qla-llc.com/webcatalog.pdf> (48 pages).
Notification of Transmittal of International Search Report and Written Opinion; Mailed Sep. 5, 2011 for corresponding PCT Application No. PCT/US2011/032099.

* cited by examiner

*Primary Examiner* — Robert R Raevis
(74) *Attorney, Agent, or Firm* — Mendelsohn, Drucker & Associates, P.C.; Edward J. Meisarosh; Steve Mendelsohn

(57) ABSTRACT

In one embodiment, a contiguous, elastic cover, for a dissolution-testing vessel, has a slit from a central opening to its outer edge. The cover may be placed around a stirring shaft by deforming the elastic cover to temporarily enlarge the slit. After returning to its original shape, the cover is placed over the vessel with the shaft free to rotate unimpeded within the central opening. The cover has a first raised annular disk on one side and a second raised annular disk on the other side, where the disks have different outer diameters to enable the cover to be used with differently sized vessels. The cover has a first opening having a first diameter and a second opening having a different, second diameter such that a conventional probe fits either at one depth within the first opening or at a different, second depth within the second opening.

21 Claims, 9 Drawing Sheets

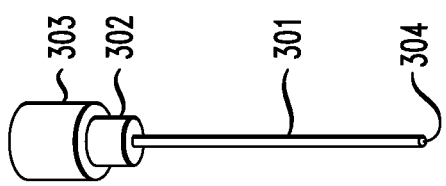
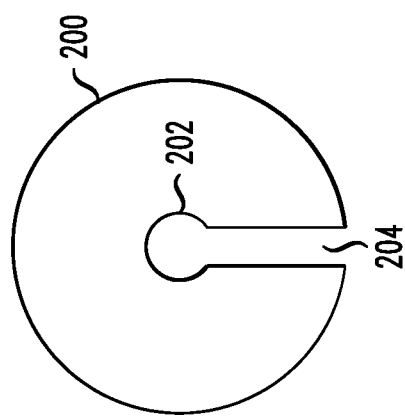
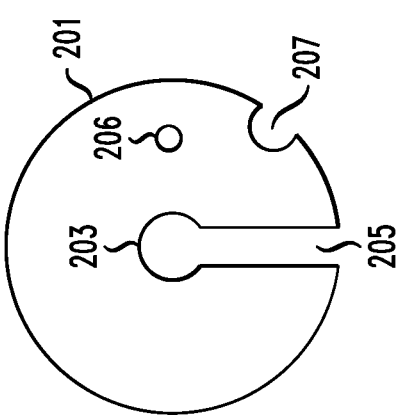
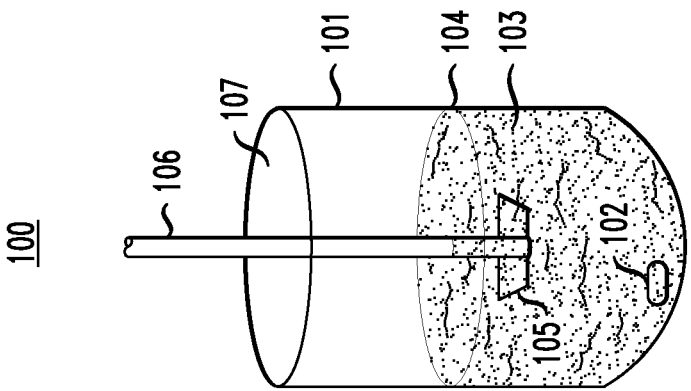

600

500

400

900

800

700

DISSOLUTION-TESTING VESSEL COVER

This application claims the benefit of the filing date of U.S. Provisional Application No. 61/323,150 filed on Apr. 12, 2010, the teachings of which are incorporated herein by reference in their entirety.

BACKGROUND OF THE INVENTION

1. Field of the Invention

The current invention relates to vessel covers, and more specifically but not exclusively, to covers for dissolution-testing vessels and the like.

2. Description of the Related Art

Dissolution testing is an important part of the process of drug discovery and pharmaceutical quality control. Dissolution testing is used to determine the rate at which a substance dissolves in a solvent. For example, dissolution testing may be used to determine the dissolution rate of a pharmaceutical product in a solution simulating, in chemical composition and temperature, fluids of the human digestive tract. Determination of the dissolution rate of pharmaceutical dosage indicates the potential availability of the pharmaceutical for absorption by patients. The dissolution rate, together with information about, for example, the solubility, permeability, and pharmacokinetics of a pharmaceutical, may be used to determine the pharmaceutical's in-vivo availability (also referred to as bio-availability). Dissolution testing may also be used to verify uniformity among production lots of a pharmaceutical. In order to allow comparison of results obtained by different apparatuses and/or at different times, standardized testing parameters are useful. A particular set of dissolution-testing parameters used for a particular test is commonly referred to as a method.

The United States Pharmacopeia (USP) is a non-governmental, official, public, standards-setting authority for prescription and over-the-counter medicines and other healthcare products manufactured or sold in the United States. The USP defines that a covered vessel must be used for pharmaceutical dissolution testing, where the vessel is made of glass or other inert transparent material. The materials should not absorb, react, or interfere with the specimen being tested. A vessel cover should be designed to prevent contamination from entering the test sample (both particle and gas) and prevent evaporative losses.

FIG. 1 shows a simplified perspective view of exemplary module 100 that is part of a conventional dissolution testing apparatus (not shown). Module 100 comprises glass vessel 101, which contains pharmaceutical 102 in solution 103, whose top surface is indicated by meniscus 104. Stirring paddle 105 is shown inside solution 103. Stirring paddle 105 is connected to and rotated by stirring shaft 106. At the top of vessel 101 is opening 107. Solution 103 is kept at a desired testing temperature, such as 37° Celsius, by means such as a water bath (not shown) or heating sleeves (not shown). At room temperature and pressure, solution 103 may experience significant evaporative loss over time if opening 107 is not covered.

FIGS. 2(A) and 2(B) show simplified top views of exemplary, conventional vessel covers 200 and 201, which are designed to cover and close opening 107 of FIG. 1. Covers 200 and 201 are made of acrylic or a similar hard plastic. Covers 200 and 201 have central openings 202 and 203, respectively, for stirring shaft 106. Covers 200 and 201 further comprise slots 204 and 205, respectively, to allow covers 200 and 201, respectively, to be placed on and/or removed from opening 107 while stirring shaft 106 is positioned in vessel 101 such that paddle 105 is inside solution 103. Cover 201 also has peripheral opening 206 and second slot 207 to allow insertion or removal of materials from vessel 101, while cover 201 remains on opening 107. The additional opening and slot of cover 201 permit, for example, (1) the use of a probe to add and/or remove samples of solution 103 and (2) the introduction of additional pharmaceuticals, without the removal of cover 201 from opening 107. However, slots 204 and 205 of covers 200 and 201, respectively, are fairly large and may allow for greater-than-desired evaporative losses or contamination potential.

FIG. 3 shows a simplified perspective view of conventional probe 300. Probe 300 comprises cannula 301, which connects to hub 302, which, in turn, connects to barrel 303. At the distal end of cannula 301 away from hub 302 is inlet 304. Note that inlet 304 may be used as either an inlet or outlet and is called an inlet herein because the more-common use of probe 300 is to extract samples of solution 103. Probe 300 may also be used, for example, to add to solution 103. The diameter of barrel 303 is larger than the diameter of hub 302 and the diameter of hub 302 is larger than the diameter of cannula 301. Barrel 303 and/or hub 302 may contain a filter (not shown) for preventing certain material from passing through probe 300.

FIG. 4 shows a simplified top view of exemplary, conventional, multi-piece vessel cover 400, designed to cover and close opening 107 of FIG. 1. Vessel cover 400 comprises first half-cover 401 and second half-cover 402, held together by hinge 403, where half-covers 401 and 402 are made of acrylic or similar rigid plastic. Hinge 403 allows half-covers 401 and 402 to swing relative to each other, as though folding vessel cover 400 approximately about the central diameter that separates half-covers 401 and 402. This folding splits apart half-covers 401 and 402 allowing the folded vessel cover 400 to be placed around stirring shaft 106. Then half-covers 401 and 402 may be brought together to form a flat disk with stirring shaft 106 in central opening 404. Half-covers 401 and 402 include peripheral openings 405 and 406, respectively, for the use of a probe or introduction of pharmaceuticals, as described above. Peripheral openings 405 and 406 may be closed with plugs (not shown) when not in use to reduce evaporative losses and contamination potential.

FIG. 5 shows a simplified top view of vessel cover 500, which is substantially similar to vessel cover 400 of FIG. 4, but with only one peripheral opening, opening 501, which corresponds to peripheral opening 405 of vessel cover 400. Peripheral opening 501 is covered with valve 502, which is made of a flexible material, such as rubber. Valve 502 is semi-permanently attached to cover 500 by tabs 504 and 505, which are attached to cover 500 by screws (not shown) or similar fasteners. Central portion 503 of valve 502 is sliced to form flaps allowing probes and pharmaceuticals to be inserted through valve 502 and peripheral opening 501. After a probe or other item is removed from valve 502, the flaps of central portion 503 are supposed to return to their original position.

FIG. 6 shows a simplified top view of exemplary, conventional, multi-piece vessel cover 600, designed to cover and close opening 107 of FIG. 1. Vessel cover 600 comprises concentric disks 601 and 602, which are attached together by rotational hinge 603 that allows disk 602 to rotate relative to disk 601. Both disks 601 and 602 have central opening 604 for stirring shaft 106. Both disks 601 and 602 are made from a rigid plastic. Disk 601 comprises peripheral openings 605 and 606 and slot 607, which are designed to function in the ways described above for peripheral openings and slots. Disk 602 includes slot 608, which is also designed to function in the way described above for slots. Disk 602 is shown as located below disk 601, where the portions of disk 602 visible through openings 605 and 606 and slot 607 are shown as striped. FIG. 6 shows disks 601 and 602 aligned so that slot 607 and openings 605 and 606 of disk 601 are occluded by disk 602. This alignment of the disks is useful for when cover 600 is in place over opening 107. Disks 602 and/or 601 may be rotated relative to each other so that slot 608 of disk 602 aligns with any one of opening 605, slot 607, and opening 606. If slot 608 is aligned with slot 607, then cover 600 may be fitted around, or removed from around, stirring shaft 106. When slot 608 is aligned with a peripheral opening, such as opening 605 or 606, then the peripheral opening may be used as described above.

FIG. 7 shows exemplary dissolution-testing module 700, which is a modification of module 100 of FIG. 1, where paddle 105 has been replaced with basket 701, stirring shaft 106 has been replaced by stirring shaft 702, and where pharmaceutical 102 is placed inside basket 701. Note that, in some systems, stirring shaft 702 may be substantially identical to stirring shaft 106, while, in other systems, stirring shaft 702 is substantially different from stirring shaft 106. Basket 701 is substantially a cylinder having a mesh wall, where the basket may be opened for the insertion of pharmaceutical samples such as pharmaceutical 102. A typical dissolution-testing basket has a removable top cap and a tight-weave mesh side wall and bottom. Other elements of module 700 are substantially the same as in module 100 and are labeled similarly. In some circumstances, it may be desired to raise or lower basket 701 while a vessel cover is in place over opening 107. Several conventional vessel covers have been described where the central opening of the covers is of a diameter appropriate to surround a stirring shaft, such as stirring shaft 106 of FIG. 1 or stirring shaft 702 of FIG. 7. Similar vessel covers may have a larger central opening that is large enough to accommodate the diameter of basket 701.

FIG. 8 shows a simplified top view of exemplary, conventional large-central-opening vessel cover 800. Cover 800 is substantially the same as cover 400 of FIG. 4, except that central opening 801 is larger than opening 404 of cover 400. In particular, central opening 801 has a diameter larger than, though similar to, the diameter of basket 701. In order to reduce evaporation losses and contamination probability because of the large central opening, a cap plug may be used in conjunction with basket 701 and vessel cover 800.

FIG. 9 shows a simplified bottom perspective view of cap plug 900, which may be used in conjunction with module 700 of FIG. 7 and vessel cover 800 of FIG. 8. Cap plug 900 is made of a rigid plastic and comprises lower disk 901 and upper disc 902. In the center of lower disk 901 is central opening 903. Upper disk 902 has a central opening whose diameter is at least as large as the diameter of central opening 903. The diameter of central opening 903 is similar to, though larger than, the diameters of stirring shafts 106 and 702 of FIG. 1 and FIG. 7, respectively. The outer diameter of lower disk 901 is similar to, though smaller than, the diameter of central opening 801 of vessel cover 800. The outer diameter of upper disk 902 is sufficiently larger than the diameter of central opening 801 so as to not be able to go through central opening 801.

Cap plug 900 may be slipped on the stirring shaft 702 of FIG. 7 when nothing is attached to the top or bottom of stirring shaft 702. When basket 701 is attached to the bottom of stirring shaft 702, the bottom of lower disk 901 of cap plug 900 rests on top of basket 701. Assuming that vessel cover 800 is positioned in opening 107 of FIG. 7 and that basket 701 and cap plug 900 are positioned above vessel cover 800, the following describes what happens as basket 701 is lowered into vessel 101. As basket 701 is lowered through opening 801, upper disk 902 of cap plug 900 comes to rest atop cover 800, with lower disk 901 resting substantially inside central opening 801. Basket 701 continues to be lowered until basket 701 is submerged in solution 103. The combination of cover 800 and cap plug 900 then provide evaporation prevention and contamination-probability minimization for dissolution-testing module 700. Basket 701 may then be raised while leaving cover 800 in place, whereupon cap plug 900 is subsequently lifted with basket 701 and rests atop basket 701.

SUMMARY OF THE INVENTION

One embodiment of the invention can be a vessel cover for dissolution-testing equipment comprising a vessel and a stirring shaft. The vessel cover is made of an elastic material. The vessel cover has an original shape having an outer circumference. The vessel cover defines a central opening having a diameter larger than the diameter of the stirring shaft. The vessel cover comprises a slit running from the central opening to the outer circumference, wherein, when the vessel cover is in the original shape, the slit has a width smaller than the diameter of the stirring shaft. The vessel cover is adapted to be temporarily deformed and then return to substantially the original shape, wherein the temporary deformation widens the slit such that the stirring shaft is allowed to pass through the temporarily widened slit and into the central opening.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 1 shows a simplified perspective view of an exemplary module that is part of a conventional dissolution testing apparatus.

FIGS. 2(A)-2(B) show simplified top views of exemplary conventional vessel covers, which are designed to cover and close the opening of FIG. 1.

FIG. 3 shows a simplified perspective view of a conventional probe.

DETAILED DESCRIPTION

The conventional vessel covers described above have various drawbacks and limitations. Some conventional vessel covers allow excessive evaporation loss and contamination probability through open slots and/or peripheral openings. Some conventional vessel covers require assembly and/or have moving mechanical parts which are liable to break down with continued use. Some conventional vessel covers use unattached plugs for peripheral openings, which may be misplaced and lost. Conventional vessel covers fit vessels of only one effective diameter, while dissolution vessels may have various effective diameters, thereby making it necessary to correlate a vessel-cover's diameter with the effective diameter of the corresponding vessel when purchasing vessel covers. Note that, although most dissolution-testing vessels have standard diameters within a narrow range, some dissolution-testing apparatuses use adapter rings or similar additional components to help hold a vessel in place. An adapter ring or a similar component used with a vessel may create a narrower effective diameter for the vessel. Novel vessel covers that address these shortcomings would be useful.

Figure 10A:
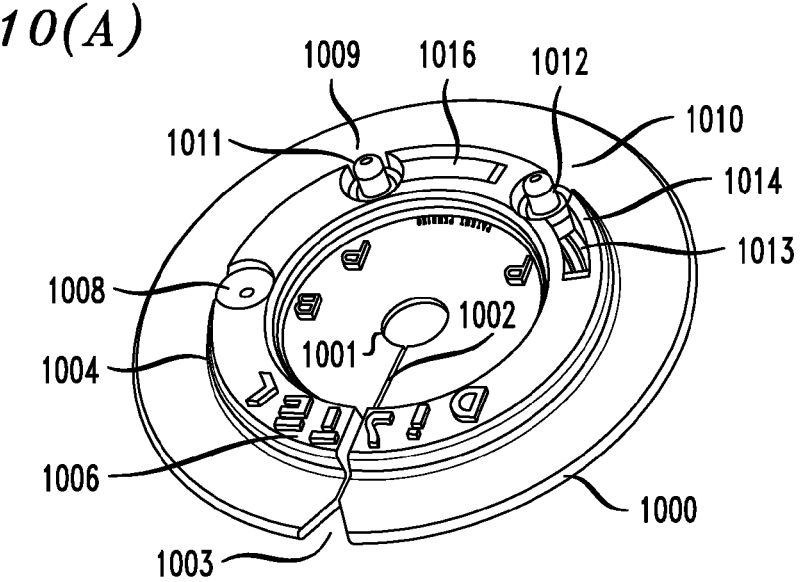
FIGS. 10(A)-10(E) show various views of a vessel cover in accordance with one embodiment of the present invention.
Figure 10B:
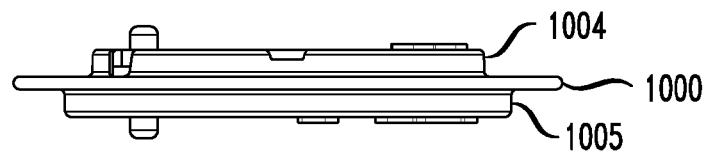
Figure 10C:
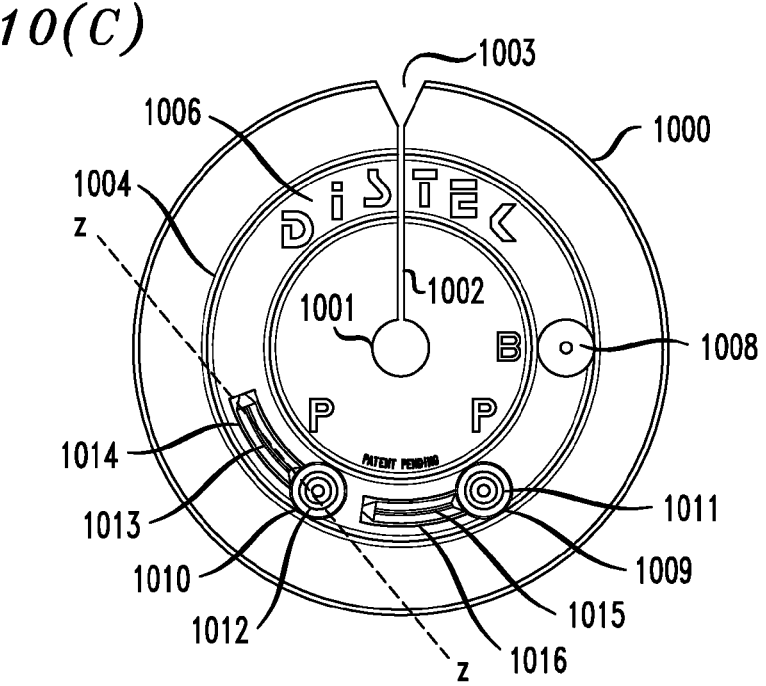
Figure 10D:
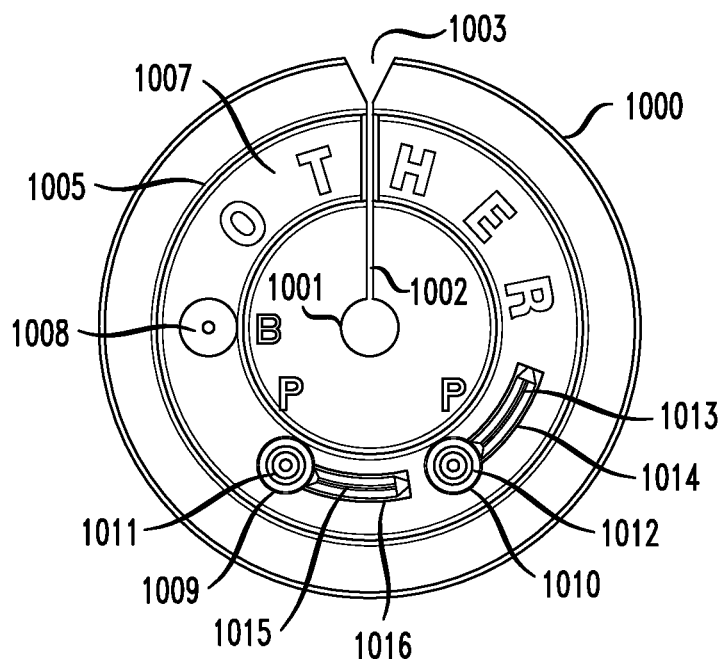
Figure 10E:
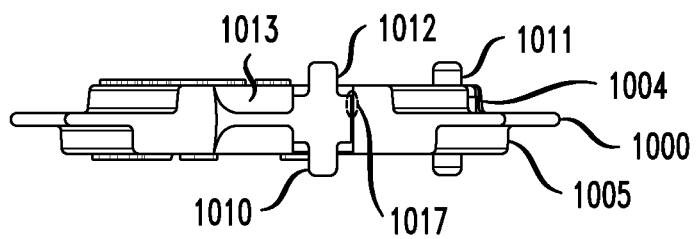

FIGS. 10(A)-10(E) show various views of vessel cover 1000 in accordance with one embodiment of the present invention. Vessel cover 1000 may be used, for example, to cover opening 107 of vessel 101 of FIG. 1. FIG. 10(A) shows a perspective view of vessel cover 1000. FIG. 10(B) shows a side view of vessel cover 1000. FIG. 10(C) shows a top view of vessel cover 1000. FIG. 10(D) shows a bottom view of vessel cover 1000. FIG. 10(E) shows a partial cross-section of vessel cover 1000 along line ZZ of FIG. 10(C). Note that the choice of "top" and "bottom" is essentially arbitrary here since, in actual use, depending on the vessel that is covered, as explained in further detail below, either side may face up or down.

Vessel cover 1000 has a unitary construction. In other words, vessel cover 1000 is a single, contiguous piece and does not use screws, glues, or other fasteners to keep its components held together. Note, however, that additional items may be attached to cover 1000 without departing from the scope of the present invention.

Vessel cover 1000 is made of an elastic material, such as silicone, and can, consequently, flex, stretch, compress, and be otherwise deformed and then return to its original shape. Examples of elastic materials include natural elastomers, such as natural rubber, and synthetic elastomers, such as rubber silicone. Vessel cover 1000 may be molded using molding techniques now known or later developed for making elastic products. Silicone material provides insulation, thereby making thermal regulation of the temperature of solution 103 easier when opening 107 is closed with vessel cover 1000.

Vessel cover 1000 includes central opening 1001, whose diameter is similar to, but larger than, the diameter of stirring shaft 106 of FIG. 1, to enable shaft 106 to rotate without interference from vessel cover 1000. Central opening 1001 is connected by slit 1002 to notch 1003. The width of slit 1002 is significantly smaller than the diameter of stirring shaft 106 in order to keep openings in vessel cover 1000 to a minimum. Slit 1002 may be created by cutting or molding vessel cover 1000 such that slit 1002 is substantially completely closed when vessel cover 1000 is at rest and not being deformed, while allowing the two sides of slit 1002 to temporarily come apart and deform when forced. Vessel cover 1000 may be placed in opening 107 and around stirring shaft 106 using a variety of methods that utilize the elasticity of vessel cover 1000. For example, notch 1003 may be placed around stirring shaft 106 and then vessel cover 1000 may be pushed in the direction from central opening 1001 to notch 1003 and, as a result, stirring shaft 106 would pass through the momentarily deformed vessel cover 1000, which is deformed around slit 1002, all the way to central opening 1001.

In another example, the two sides of slit 1002 may be scissored, where cover 1000 is deformed with (a) one side of vessel cover 1000 adjacent to slit 1002 pushed down and (b) the other side of vessel cover 1000 adjacent to slit 1002 pushed up to enlarge the gap of slit 1002, whereupon stirring shaft 106 may be easily passed all the way to central opening 1001 through the enlarged gap. Corresponding methods, but performed in reverse, may be used to remove vessel cover 1000 from around stirring shaft 106. Note that, if stirring shaft 106 is not positioned in opening 107, then vessel cover 1000 may simply be placed in opening 107 without requiring any forced deformation.

Vessel cover 1000 is shaped substantially as a flat disk having various hollowed and raised features. Note that, although individually identified, these features are part of the contiguous, unitary vessel cover 1000. The top side of vessel cover 1000 comprises annular disk 1004, which is (i) concentric with the outer circumference of vessel cover 1000 and central opening 1001, (ii) a raised washer-shaped feature, and (iii) visible in FIGS. 10(A), 10(B), 10(C), and 10(E). The bottom side of vessel cover 1000 comprises annular disk 1005, which is (i) also concentric with the outer circumference of vessel cover 1000 and central opening 1001, (ii) also a raised washer-shaped feature, and (iii) is visible in FIGS. 10(B), 10(D) and 10(E). Both disks 1004 and 1005 are split by slit 1002. Disks 1004 and 1005 serve various functions, such as providing additional rigidity to vessel cover 1000 and providing an appropriate fit in the opening of a corresponding vessel.

As noted above, dissolution-testing vessels may have a variety of effective diameters and, as a result, may have differently sized, corresponding openings. Vessel cover 1000 of FIGS. 10(A)-10(E) is a reversible vessel cover designed to fit inside at least two different types of vessels having different effective diameters. Note that the outside diameters of disks 1004 and 1005 are different, where the outside diameter of disk 1005 is larger than the outside diameter of disk 1004. Disk 1005 has an outside diameter designed to fit snugly inside the vessel opening of vessels provided by, for example, Distek, Inc., of North Brunswick, N.J. This is indicated by label 1006 of FIGS. 10(A) and 10(C), where label 1006 is embossed on disk 1004. Label 1006 reads "Distek" and thereby indicates to a user that, with label 1006 visible, vessel cover 1000 will fit snugly over and within the opening of a Distek vessel. In other words, label 1006 on disk 1004 on the top side of vessel cover 1000 identifies vessel types corresponding to the outside diameter of disk 1005 on the bottom side of vessel cover 1000.

Disk 1004 has an outside diameter designed to fit inside the effective opening of vessels provided by one or more providers other than Distek. This is indicated by label 1007 of FIG. 10(D), where label 1007 is embossed on disk 1005. Label 1007 reads "Other" and thereby indicates that, with label 1007 visible, vessel cover 1000 will fit over and in the effective opening of a non-Distek vessel. In other words, label 1007 on disk 1005 on the bottom side of vessel cover 1000 identifies and corresponds to the outside diameter of disk 1004 on the top side of cover 1000.

Vessel cover 1000 comprises peripheral openings 1008, 1009, and 1010 for use with probes such as probe 300 of FIG. 3. Peripheral openings 1008, 1009, and 1010 (i) extend through disks 1004 and 1005 and (ii) are visible in FIGS.

10(A), 10(C), and 10(D). Note that openings 1009 and 1010 are shown in FIGS. 10(A), 10(C), and 10(D) plugged by plugs 1011 and 1012, respectively. Opening 1008 is designed for solution-sample extraction by probe 300 of FIG. 3 in conjunction with basket-comprising module 700 of FIG. 7, as indicated by the letter "B," for "basket," next to opening 1008. Note that, as discussed below, vessel cover 1000 may be used in conjunction with basket-comprising module 700. Openings 1009 and 1010 are designed for solution-sample extraction by probe 300 of FIG. 3 in conjunction with paddle-comprising module 100 of FIG. 1, as indicated by the letters "P," for "paddle," next to openings 1009 and 1010.

Opening 1008 has a different diameter from openings 1009 and 1010, which, in conjunction with the different component diameters of probe 300 of FIG. 3, allows for the setting of different penetration depths for inlet 304 through vessel cover 1000. Setting different penetration depths for inlet 304 is useful for complying with USP standards, which call for particular and different depths at which solution samples should be extracted, depending on whether the corresponding test method uses a paddle or a basket.

The diameter of opening 1008 is similar to, though larger than, the diameter of cannula 301 of probe 300. Cannula 301 can, consequently, easily pass through opening 1008. Note that opening 1008 is located in circular recesses in disks 1004 and 1005, where the diameter of the recesses is sufficient to accommodate hub 302. The diameter of opening 1008 is sufficiently smaller than the diameter of hub 302 of probe 300 to prevent hub 302 from passing through opening 1008. Consequently, inserting probe 300 into opening 1008 with vessel cover 1000 in opening 107 of FIG. 1 will result in having inlet 304 at a depth past opening 107 that is substantially equal to the length of cannula 301 that extends past hub 302, adjusted by the depth of the recess around opening 1008. Designing different depths of the recesses around opening 1008 will change the penetration depth of inlet 304. The penetration depth of inlet 304 can also be changed by designing different lengths of cannula 301.

Below is a descriptions of features of opening 1010. Note that the same applies to opening 1009. The diameter of opening 1010 is similar to, though larger than, the diameter of hub 302 of FIG. 3. Cannula 301 and hub 302 can, consequently, easily pass through opening 1010. The diameter of opening 1010 is sufficiently smaller than the diameter of barrel 303 to prevent barrel 303 from passing through opening 1010. Consequently, inserting probe 300 into opening 1010 with vessel cover 1000 positioned in opening 107 of FIG. 1 will result in having inlet 304 at a depth past opening 107 that is substantially equal to the length of cannula 301 that extends past hub 302 plus the height of hub 302, minus the height of whichever of disk 1004 and disk 1005 that barrel 303 would be contacting. Designing different heights of disks 1004 and/or 1005 changes the penetration depth of inlet 304. Note that, in an alternative embodiment, opening 1010 is located in a circular recess (not shown), where the diameter of the recess is sufficient to accommodate barrel 303. Designing different depths of the recesses around opening 1010 may be used to change the penetration depth of inlet 304.

Opening 1010 may be selectively closed with plug 1012. Plug 1012 has a cylindrical central portion (a) whose diameter is slightly smaller than the diameter of opening 1010 and (b) pull tabs on top and bottom of the central portion. In one implementation, the diameter of plug 1012 is approximately 0.5 mm smaller than the diameter of opening 1010. The outer diameter of plug 1012 is such that, as explained below, plug 1012 will (a) stay in place due to static friction with the inner surface of opening 1010 when subject to only the force of gravity and (b) be removable from opening 1010 when a user pulls on either pull tab of plug 1012. Plug 1012 is connected to the rest of vessel cover 1000 via tail 1013. Tail 1013 is substantially a flat arcuate band positioned in the center, vertically, of arcuate opening 1014. Arcuate opening 1014 is connected to opening 1010 and extends through both disk 1004 and disk 1005. Arcuate tail 1013 and arcuate opening 1014 correspond to an arc of a circle concentric with the outer circumference of vessel cover 1000. The width of opening 1014 is similar to, though larger than, the width of tail 1013 to enable tail 1013 to swing up and down within opening 1014.

A cross section of plug 1012 and tail 1013 is shown in FIG. 10(E). Tail 1013 allows plug 1012 to be swung clockwise or counterclockwise, as seen in FIG. 10(E), out of opening 1010, thereby clearing opening 1010 and allowing for the insertion of probe 300 of FIG. 3 into opening 1010. Swinging plug 1012 out of opening 1010 requires a force greater than the force of gravity. This force may be provided, for example, by a user pulling on either pull tab of plug 1012. The force of gravity alone is not sufficient to pull plug 1012 out of opening 1010. Tail 1013 restricts plug 1012 to motion in an arc. When plug 1012 is in opening 1010, as shown in FIG. 10(E), gravity pulls plug 1012 down while tail 1013 prevents plug 1012 from falling straight down. This interaction creates contact and static friction between plug 1012 and the inside surface of opening 1010 in, for example, area 1017. As noted above, this static friction may be overcome by, for example, pulling on the pull tabs of plug 1012, where the pulling may also temporarily deform tail 1013, plug 1012, and/or opening 1010. Since plug 1012 is a part of vessel cover 1000, attached by tail 1013, plug 1012 is not likely to be misplaced or get lost. Plug 1011 in opening 1009 and tail 1015 in arcuate opening 1016 function in substantially the same way as described above for plug 1012, opening 1010, tail 1013, and arcuate opening 1014, respectively.

FIGS. 11(A)-11(D) show various views of vessel cover 1100 in accordance with another embodiment of the present invention. Vessel cover 1100 is substantially similar in many respects to the above-described vessel cover 1000 of FIGS. 10(A)-10(E). Similar components are similarly labeled, but with a different prefix. Elements of vessel cover 1100 that function in substantially the same way as the corresponding elements of vessel cover 1000 are not described further below. Described below are elements of vessel 1100 that are different from, or have no, corresponding elements in vessel cover 1000.

In addition to slit 1102, which corresponds to slit 1002 of FIG. 10(A), vessel cover 1100 has three shorter slits 1120, which extend from central opening 1101 to near the inner circumference of disks 1104 and 1105. Slit 1102 and slits 1120 create four flexible flaps in the center of vessel cover 1100, which allow for the passage of, for example, basket 701 of FIG. 7 through vessel cover 1100 without removing vessel cover 1100 from opening 107 of FIG. 7. Note that moving basket 701 up through vessel cover 1100 may require holding down vessel cover 1100 in place so as to prevent vessel cover 1100 from going up together with basket 701. During the passage of basket 701, the flaps created by slits 1102 and 1120 flex and deform and then, after the passage of basket 701, the flaps return to their original position and, thereby, provide thermal insulation, contamination protection, and evaporation prevention.

Instead of plugs, tails, and arcuate openings as in vessel cover 1000 of FIG. 10(A), peripheral openings 1109 and 1110 of vessel cover 1100 use flaps to both (i) provide the benefits of a vessel cover and (ii) allow appropriate access to probe 300 of FIG. 3. The flaps of openings 1109 and 1110 are integral components of vessel cover 1100 and are formed by the slits shown. The flaps of openings 1109 and 1110 flex to allow hub 302 of probe 300 through and then return to their original, closed position, when hub 302 is removed.

Figure 6:
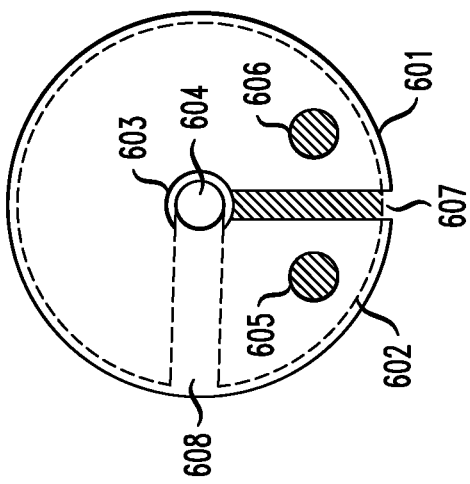
FIG. 6 shows a simplified top view of an exemplary, conventional, multi-piece vessel cover, designed to cover and close the opening of FIG. 1.
Figure 5:
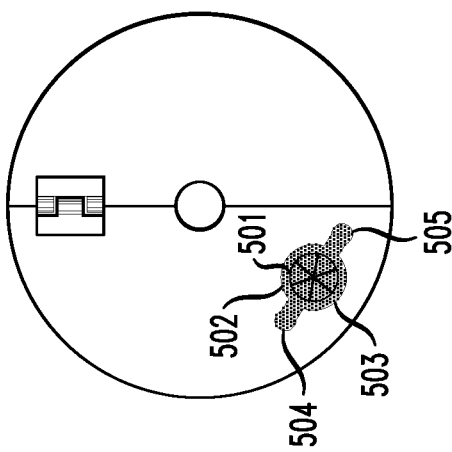
FIG. 5 shows a simplified top view of a vessel cover, which is substantially similar to the vessel cover of FIG. 4, but with only one peripheral opening.
Figure 4:
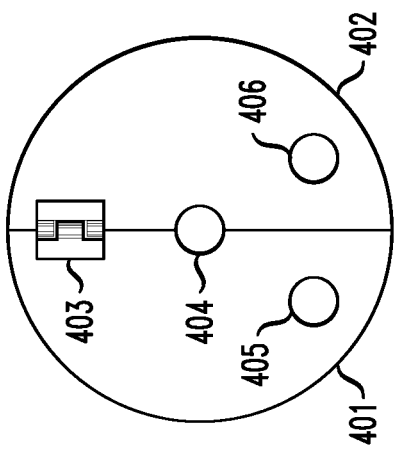
FIG. 4 shows a simplified top view of an exemplary, conventional, multi-piece vessel cover, designed to cover and close the opening of FIG. 1.
Figure 9:
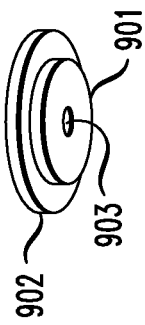
FIG. 9 shows a simplified bottom perspective view of a cap plug, which may be used in conjunction with the module of FIG. 7 and the vessel cover of FIG. 8.
Figure 8:
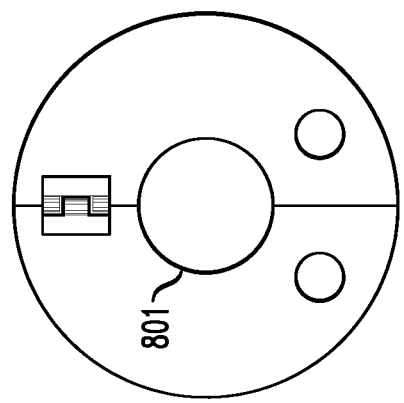
FIG. 8 shows a simplified top view of a large-central-opening vessel cover.
Figure 7:
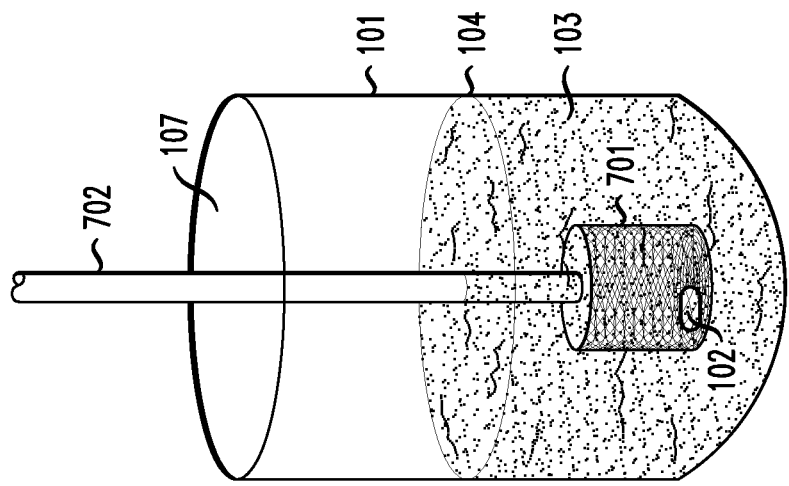
FIG. 7 shows an exemplary dissolution-testing module, which is a modification of the module of FIG. 1.

Basket 701 of FIG. 7 has been described as substantially a tight-weave mesh cylinder. In alternative embodiments, different kinds of baskets are used. For example, in one alternative embodiment, a loose-weave mesh is used. In another alternative embodiment, a cage-like basket is used.

Figure 11A:
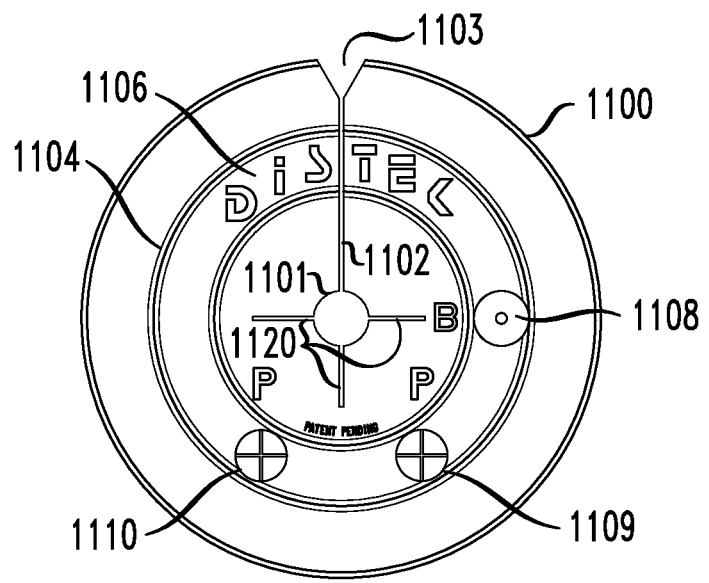
FIGS. 11(A)-11(D) show various views of a vessel cover in accordance with another embodiment of the present invention.

Embodiments of the invention have been described where the part of the slit by the outer circumference of the vessel cover comprises a notch such as notch 1003 of FIG. 10(A) and notch 1103 of FIG. 11(A). It should be noted that the notch is not mandatory. In alternative embodiments, the vessel cover does not have a notch. Instead, the slit extends, notch-less, to the outer circumference of the vessel cover.

Embodiments of the invention have been described where one side of the vessel cover has been described as fitting inside one or more non-Distek vessel setups. In some alternative embodiments, both sides fit non-Distek vessel setups. In some alternative embodiments, a non-Distek side is designed to fit snugly within one particular kind of vessel setup, where the kind of vessel setup may be identified with a label more specific than "Other."

Embodiments of the invention have been described where labels on vessel covers identifying corresponding vessel types are embossed written labels. In alternative embodiments, other kinds of labels are used. For example, labels may be printed and/or may be in the form of colors or pictures.

Embodiments of the invention have been described where each side of the vessel cover has one raised disk. In some alternative embodiments, at least one side has a plurality of disks having different diameters and different heights allowing for a snug fit over a plurality of different types of vessels having different sized openings. In some alternative embodiments, only one side of the vessel cover has a raised disk for fitting into a corresponding type of vessel.

FIGS. 12(A)-12(D) show various views of vessel cover 1200 in accordance with one of the above-described embodiments. Vessel cover 1200 is substantially similar in many respects to the above-described vessel cover 1100 of FIGS. 11(A)-11(D). Components of vessel cover 1200 similar to corresponding components of vessel cover 1100 are similarly labeled, but with a prefix of "12" instead of "11." Consequently, elements of vessel cover 1200 that are substantially the same as the corresponding elements of vessel cover 1100 are not described further herein. Vessel cover 1200 includes third annular disk 1221 located on top of disk 1205, where, as noted, disk 1205 corresponds to disk 1105 of FIGS. 11(A)-11(D). Disk 1221 has an outer diameter different from the outer diameters of disks 1204 and 1205 and is designed to snugly fit vessels having correspondingly sized openings.

An embodiment of the invention has been described where arcuate tail 1013 and arcuate opening 1014 of FIG. 10(C) correspond to an arc of a circle concentric with the outer circumference of vessel cover 1000. In one alternative embodiment, arcuate tail 1013 and arcuate opening 1014 correspond to an arc other than an arc of a circle concentric with the outer circumference of vessel cover 1000. In another alternative embodiment, tail 1013 and opening 1014 are not arcuate but, rather, have a non-arcuate shape when viewed from above or below.

In one alternative embodiment of vessel cover 1000 of FIGS. 10(C)-10(D), the diameter of central opening 1001 is larger than the diameter of basket 701 of FIG. 7, thereby allowing basket 701 to be raised and lowered through vessel cover 1000. In one alternative embodiment of vessel cover 1100 of FIGS. 11(A)-11(B), slits 1120 are not needed since the diameter of central opening 1101 is larger than the diameter of basket 701 of FIG. 7, thereby allowing basket 701 to be raised and lowered through vessel cover 1100. Cap plug 900 may be used in conjunction with these embodiments. Cap plug 900 has been described as made of a rigid plastic. A similarly shaped cap plug, but made of an elastic material, may instead be used with the above-described embodiments. In another alternative embodiment of vessel cover 1100, there are no slits 1120. This embodiment is useful in conjunction with module 100 of FIG. 1. In one alternative embodiment of vessel cover 1100, peripheral openings 1109 and 1110 are replaced by plugged openings such as openings 1009 and 1010 of vessel cover 1000 with the accompanying plugs, tails, and arcuate openings.

Figure 11B:
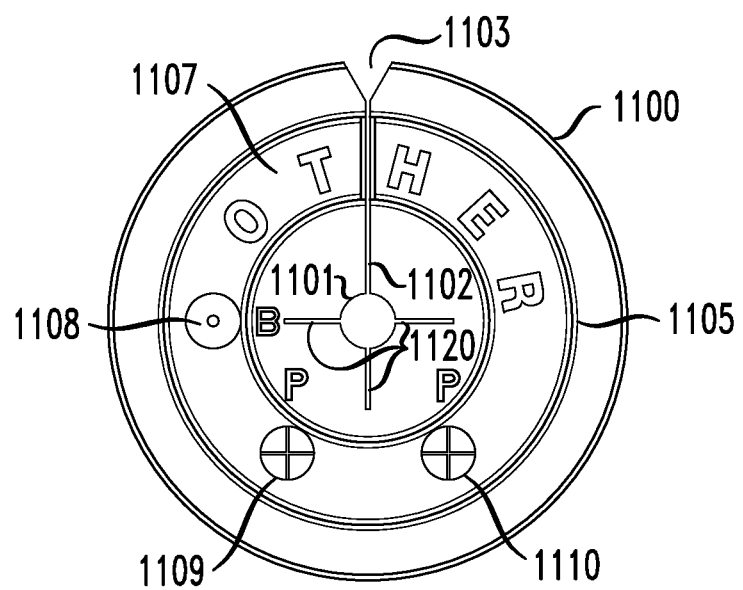
Figure 11C:
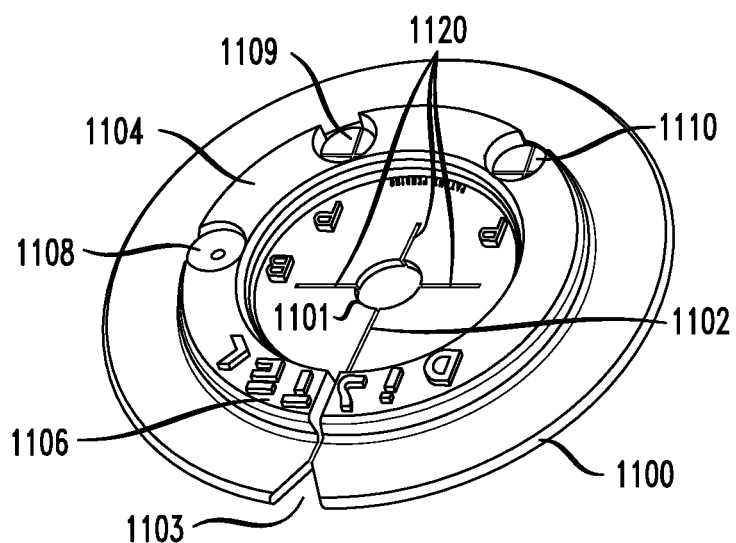
Figure 11D:
Figure 12A:
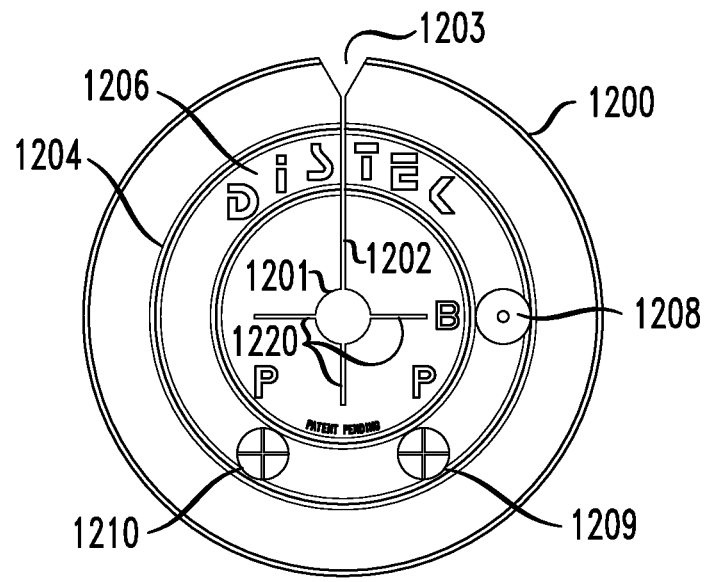
FIGS. 12(A)-12(D) show various views of a vessel cover in accordance with yet another embodiment.
Figure 12B:
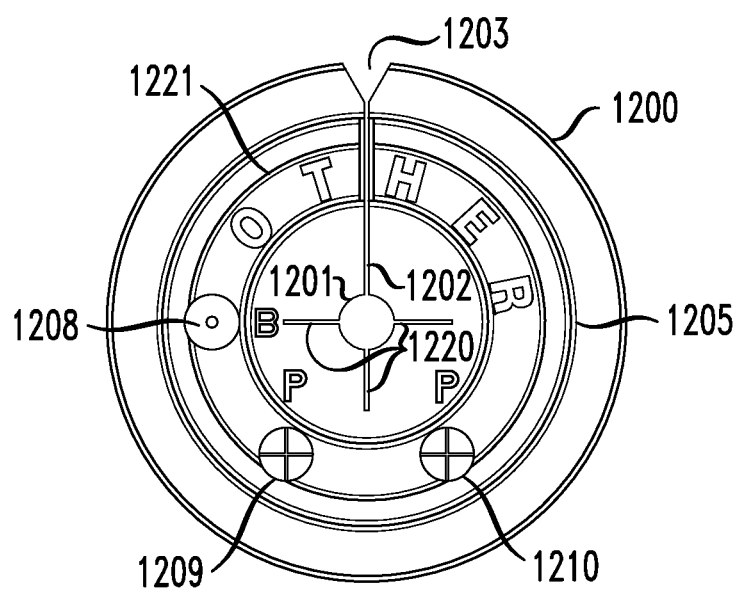
Figure 12C:
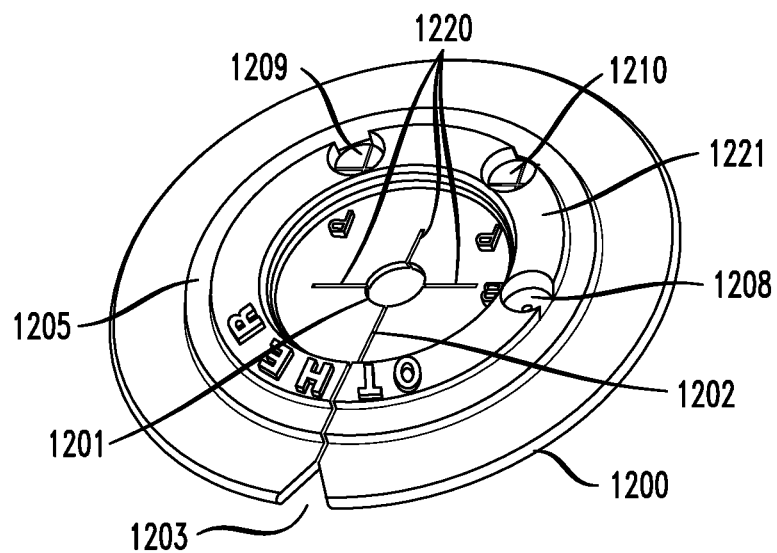
Figure 12D:
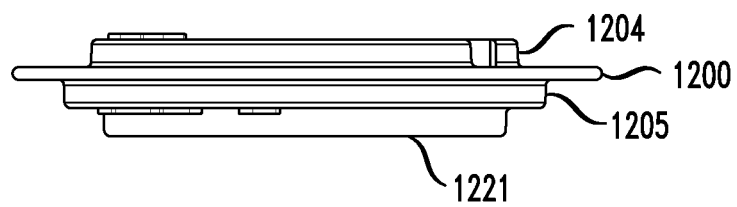

Vessel cover 1100 of FIGS. 11(A)-11(B) has been described as having openings closable with four flaps. In alternative embodiments, one or more of the openings have a different number of flaps.

Vessel covers have been described as having two openings for use with dissolution-testing modules with paddles. In some alternative embodiments, the vessel cover has a different number of openings for use with dissolution-testing modules with paddles. Embodiments of the invention have been described where the vessel cover uses either plugs or flaps for openings for use with dissolution-testing modules with paddles. In some alternative embodiments, the vessel cover has at least one of each type of opening.

It will be further understood that various changes in the details, materials, and arrangements of the parts which have been described and illustrated in order to explain the nature of this invention may be made by those skilled in the art without departing from the scope of the invention as expressed in the following claims.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Unless explicitly stated otherwise, each numerical value and range should be interpreted as being approximate as if the word "about" or "approximately" preceded the value of the value or range. As used in this application, unless otherwise explicitly indicated, the term "connected" is intended to cover both direct and indirect connections between elements.

The use of figure numbers and/or figure reference labels in the claims is intended to identify one or more possible embodiments of the claimed subject matter in order to facilitate the interpretation of the claims. Such use is not to be construed as limiting the scope of those claims to the embodiments shown in the corresponding figures.

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

Although the steps in the following method claims are recited in a particular sequence with corresponding labeling, unless the claim recitations otherwise imply a particular sequence for implementing some or all of those steps, those steps are not necessarily intended to be limited to being implemented in that particular sequence.

We claim:

1. A vessel cover for dissolution-testing equipment comprising a vessel and a stirring shaft, wherein:
   the vessel cover is made of an elastic material;
   the vessel cover has an original shape having an outer circumference;
   the vessel cover defines a central opening having a diameter larger than the diameter of the stirring shaft;
   the vessel cover comprises a slit running from the central opening to the outer circumference, wherein, when the vessel cover is in the original shape, the slit has a width smaller than the diameter of the stirring shaft; and
   the vessel cover is adapted to be temporarily deformed and then return to substantially the original shape, wherein the temporary deformation widens the slit such that the stifling shaft is allowed to pass through the temporarily widened slit and into the central opening.

2. The vessel cover of claim 1, wherein the vessel cover has a notch at the end of the slit at the outer circumference of the vessel cover.

3. The vessel cover of claim 2, wherein the opening of the notch is larger than the diameter of the stifling shaft.

4. The vessel cover of claim 1, wherein the elastic material is silicone.

5. The vessel cover of claim 1, wherein:
   the vessel cover comprises a first side and a second side;
   the first side comprises a first annular disk that is (i) a raised feature concentric with the central opening and (ii) split by the slit; and
   the outer diameter of the first annular disk is designed to fit a first vessel-setup type.

6. The vessel cover of claim 5, wherein the second side comprises a first label identifying the first vessel-setup type.

7. The vessel cover of claim 5, wherein:
   the second side comprises a second annular disk that is (i) a raised feature concentric with the central opening and (ii) split by the slit; and
   the outer diameter of the second annular disk is:
      different from the outer diameter of the first annular disk; and
      designed to fit a second vessel-setup type different from the first vessel-setup type.

8. The vessel cover of claim 7, wherein the first side comprises a second label identifying the second vessel-setup type.

9. The vessel cover of claim 5, wherein:
   the first side further comprises a third annular disk that is (i) a raised feature above the first annular disk, (ii) concentric with the central opening and split by the slit; and
   the outer diameter of the third annular disk is designed to fit a third vessel-setup type different from the first vessel-setup type.

10. The vessel cover of claim 1, wherein:
    the dissolution testing equipment further comprises a probe;
    the probe comprises:
       a cannula having a cannula diameter and an inlet;
       a hub connected to the cannula and having a hub diameter larger than the cannula diameter; and
       a barrel connected to the hub and having a barrel diameter larger than the hub diameter;
    the vessel cover further comprises:
       a first peripheral opening having a diameter that is both larger than the cannula diameter and sufficiently smaller than the hub diameter to prevent entry of the hub into the first peripheral opening, such that inserting the probe in the first peripheral opening results in a first penetration depth for the inlet; and
       a second peripheral opening having a diameter that is both larger than the hub diameter and sufficiently smaller than the barrel diameter to prevent entry of the barrel into the second peripheral opening, such that inserting the probe in the second peripheral opening results in a second penetration depth for the inlet different from the first penetration depth.

11. The vessel cover of claim 10, wherein:
    the vessel cover comprises a first side and a second side;
    the first side comprises a first annular disk that is (i) a raised feature concentric with the central opening and (ii) split by the slit;
    the second side comprises a second annular disk that is (i) a raised feature concentric with the central opening and (ii) split by the slit;
    the first peripheral opening is located within a first circular recess in the first annular disk and a second circular recess in the second annular disk; and
    the diameters of the first and second circular recesses are each larger than the hub diameter.

12. The vessel cover of claim 10, wherein the vessel cover further comprises:
    a first plug for selectively plugging the second peripheral opening, the first plug comprising a central portion having substantially the same cross section as the second peripheral opening; and
    a first-tail opening that (i) is connected to the second peripheral opening and (ii) houses a first tail connected between the central portion of the first plug and a wall of the first-tail opening so that the first plug may swing in and out of the second peripheral opening, with the first tail swinging correspondingly within the first-tail opening, so that the first plug selectively plugs or unplugs the second peripheral opening.

13. The vessel cover of claim 12, wherein the vessel cover further comprises:
    a third peripheral opening substantially similar to the second peripheral opening;
    a second plug for selectively plugging the third peripheral opening, the second plug comprising a central portion having substantially the same cross section as the third peripheral opening; and
    a second-tail opening that (i) is connected to the third peripheral opening and (ii) houses a second tail connected between the central portion of the second plug and a wall of the second-tail opening so that the second plug may swing in and out of the second peripheral opening, with the second tail swinging within the second-tail opening, so that the second plug selectively plugs or unplugs the third peripheral opening.

14. The vessel cover of claim 13, wherein the vessel cover is a contiguous vessel cover having unitary construction.

15. The vessel cover of claim 12, wherein the first tail and first-tail opening correspond to an arc of a circle concentric with the central opening of the vessel cover.

16. The vessel cover of claim 12, wherein:
    there is sufficient static friction between the first plug and the inside of the second peripheral opening to keep the first plug from swinging out of the second peripheral opening due to the force of gravity;
    the static friction is not sufficient to prevent a user from forcing the first plug out of the second peripheral opening.

17. The vessel cover of claim 12, wherein the first plug further comprises first and second pull tabs connected to the top and bottom, respectively, of the central portion of the first plug, the first and second pull tabs adapted to be used to pull the first plug out of the second peripheral opening from corresponding sides of the vessel cover.

18. The vessel cover of claim 10, wherein the vessel cover further comprises a plurality of additional slits radiating from the central opening that do not extend to the outer circumference of the vessel cover.

19. The vessel cover of claim 10, wherein the second peripheral opening comprises integral flaps adapted to:
   substantially occlude the second peripheral opening;
   flex out of the way of the probe to allow the insertion of the probe hub; and
   return to substantially occluding the second peripheral opening upon removal of the probe hub.

20. The vessel cover of claim 1, wherein:
   the dissolution-testing equipment further comprises a substantially cylindrical basket adapted to attach to the stifling shaft;
   the outside diameter of the basket is larger than the diameter of the stirring shaft;
   the diameter of the central opening is larger than the outside diameter of the basket; and
   the dissolution-testing equipment further comprises a cap plug positioned around the stifling shaft and adapted to selectively plug the central opening.

21. The vessel cover of claim 1, wherein the vessel cover is a contiguous vessel cover having unitary construction.

* * * * *

UNITED STATES PATENT AND TRADEMARK OFFICE
CERTIFICATE OF CORRECTION

PATENT NO. : 8,434,378 B2  
APPLICATION NO. : 13/085064  
DATED : May 7, 2013  
INVENTOR(S) : Jeffrey Brinker et al.

Page 1 of 1

It is certified that error appears in the above-identified patent and that said Letters Patent is hereby corrected as shown below:

In the Claims:

- In Column 11, Claim 1, Line 16, please replace "stifling" with --stirring--; Claim 3, Line 22, please replace "stifling" with --stirring--; Claim 9, Line 48, please insert --(iii)-- before "split".

- In Column 13, Claim 20, Lines 16-17, please replace "stifling" with --stirring--; Claim 20, Line 23, please replace "stifling" with --stirring--.

Signed and Sealed this  
Thirtieth Day of July, 2013

Teresa Stanek Rea  
*Acting Director of the United States Patent and Trademark Office*